United States Patent
Zibold et al.

(10) Patent No.: US 9,470,646 B2
(45) Date of Patent: Oct. 18, 2016

(54) CAPACITIVE LOCATING APPLIANCE HAVING OPPOSING ELECTRODES

(71) Applicant: Robert Bosch GmbH, Stuttgart (DE)

(72) Inventors: Tobias Zibold, Stuttgart (DE); Andrej Albrecht, Leinfelden-Echterdingen (DE)

(73) Assignee: Robert Bosch GmbH, Stuttgart (DE)

( * ) Notice: Subject to any disclaimer, the term of this patent is extended or adjusted under 35 U.S.C. 154(b) by 31 days.

(21) Appl. No.: 14/388,987

(22) PCT Filed: Feb. 14, 2013

(86) PCT No.: PCT/EP2013/052919
§ 371 (c)(1),
(2) Date: Sep. 29, 2014

(87) PCT Pub. No.: WO2013/143761
PCT Pub. Date: Oct. 3, 2013

(65) Prior Publication Data
US 2015/0015231 A1 Jan. 15, 2015

(30) Foreign Application Priority Data
Mar. 29, 2012 (DE) .......... 10 2012 205 097

(51) Int. Cl.
*G01N 27/22* (2006.01)
*G01V 3/08* (2006.01)

(52) U.S. Cl.
CPC .............. *G01N 27/22* (2013.01); *G01V 3/088* (2013.01)

(58) Field of Classification Search
CPC .............................. G01N 27/22; G01V 3/088
USPC ................... 324/67, 326–329, 663; 340/562
See application file for complete search history.

(56) References Cited

U.S. PATENT DOCUMENTS

2014/0239981 A1* 8/2014 Zibold .............. G01V 3/02
324/680

FOREIGN PATENT DOCUMENTS

| DE | 10 2007 012 111 A1 | 10/2007 |
| DE | 10 2007 058 088 A1 | 6/2009 |
| DE | 10 2008 005 783 A1 | 7/2009 |

OTHER PUBLICATIONS

International Search Report corresponding to PCT Application No. PCT/EP2013/052919, mailed Jun. 5, 2013 (German and English language document) (6 pages).

*Primary Examiner* — Jay Patidar
(74) *Attorney, Agent, or Firm* — Maginot, Moore & Beck LLP

(57) ABSTRACT

A locating appliance for a capacitive detection of an object encloses in a medium. The locating appliance comprises a measurement electrode such that a first alternating current flows from the measurement electrode into the medium. The locating appliance further comprises a reception electrode where the measurement electrode forms a measurement capacitance with the reception electrode, where the measurement capacitance is based at least in part on the object. The locating appliance further comprises a reference electrode such that the reference electrode forms a reference capacitance with the reception electrode, where the reference capacitance is not based on the object. The locating appliance further comprises a first opposing electrode that is configured to introduce a first alternating current in the medium. The absolute value of the second alternating current corresponds to an absolute value of the first alternating current and is in antiphase with the second alternating current.

13 Claims, 4 Drawing Sheets

CAPACITIVE LOCATING APPLIANCE HAVING OPPOSING ELECTRODES

This application is a 35 U.S.C. §371 National Stage Application of PCT/EP2013/052919, filed on Feb. 14, 2013, which claims the benefit of priority to Serial No. DE 10 2012 205 097.3, filed on Mar. 29, 2012 in Germany, the disclosures of which are incorporated herein by reference in their entirety.

The disclosure relates to a locating appliance. In particular, the disclosure relates to a locating appliance for the capacitive detection of an object enclosed in a medium.

BACKGROUND

In order to sense an article concealed in a wall, for example a beam in a wall of lightweight construction, capacitive detectors are known. Such detectors use an electrode that has its charging or discharge behavior determined in order to infer the dielectric object. Detectors having a plurality of electrodes are also known, which involve determining a change in the capacitance of a pair of electrodes. Usually, it is necessary for such detectors to be calibrated manually on the wall, since the appliances cannot detect wall contact themselves and the capacitance of the electrodes or electrode pairs is dependent on ambient conditions, such as a temperature, a humidity, an object averted from the sensor, grounding via a user or electrical or dielectric properties of the wall material. In order to take account of these variable influencing factors, it is necessary for known appliances to be calibrated on the wall, which requires either appropriate control by a user or a complex sensor system.

DE 10 2007 058 088 A1 shows a sensor for locating dielectric objects in a medium. The sensor shown determines a ratio between a reference capacitance and a measurement capacitance, the latter being dependent on the position of the object in relation to electrodes of the two capacitances.

DE 10 2008 005 783 B4 shows a capacitive detector as a crash protection system that uses a push-pull measurement bridge to compare the capacitance of two capacitances with one another. One of the capacitances is formed by two electrodes that can be positioned relative to one another, so that a change in their relative interval can be used to generate a signal that warns of crashing.

The disclosure is based on the object of specifying a locating appliance for capacitive detection that does not require calibration in order to attain a high level of measurement accuracy.

SUMMARY

The disclosure achieves this object by means of a locating appliance having the features of the independent claim. Subclaims reproduce preferred embodiments.

There are essentially two reasons for requiring calibration of the locating appliance. Firstly, uncontrollable influences, such as an ambient temperature, an ambient humidity, an object averted from the sensor or grounding of the locating appliance via a user, can influence the output signal. Secondly, the output signal differs, regardless of the object against a medium, from an output signal in air, with a material and a material thickness of the medium and also electrical wall properties, such as a dielectric constant or a conductivity, being able to be included in the output signal.

An inventive locating appliance for the capacitive detection of an object enclosed in a medium comprises a measurement electrode, a reception electrode and a reference capacitance connected to the reception electrode. In this case, the measurement electrode forms, with the reception electrode, a measurement capacitance that can be influenced by the object, whereas the reference capacitance cannot be influenced by the object. In addition, an opposing electrode is provided that is set up to introduce an alternating current into the medium, the absolute value and phase of said alternating current corresponding to those of an alternating current that flows from the measurement electrode into the medium.

The opposing electrode can minimize or compensate for currents that distort a measurement result. In particular, an influence of a user of the locating appliance on the measurement may be minimized. Operation of the locating appliance may therefore be independent of how the user uses the appliance and to what extent or in what way the user is grounded, that is to say electrically coupled to the medium. This allows the object to be determined without having to calibrate the locating appliance prior to a measurement.

Preferably, the reference capacitance is formed from a reference electrode and the reception electrode.

The opposing electrode can form a capacitance with the medium in order to introduce the alternating current into the medium capacitively. To this end, the opposing electrode may be arranged close to the medium and DC-isolated therefrom. In particular, the opposing electrode may be arranged close to the measurement electrode and designed in a similar manner thereto. The capacitive coupling of the opposing electrode to the medium can be used advantageously particularly in the case of an inhomogeneous or uneven medium, since electrical contact with the medium is not necessary.

Alternatively, or in addition, the opposing electrode may also be resistively coupled to the medium in order to introduce the alternating current into the medium by direct electrical connection. As a result, a surface of the opposing electrode may have relatively small dimensions, for example.

In a preferred embodiment, the locating appliance also comprises two AC voltage sources in antiphase, the first of which is connected to the measurement electrode and the second of which is connected to the reference capacitance, and a third AC voltage source for applying to the opposing electrode a signal that is in antiphase with the voltage on the measurement electrode and has an amplitude that is proportional thereto.

In this way, it is possible to compensate for different levels of coupling of the measurement electrode and the opposing electrode in each case to the medium. This allows improved determination of the object, for example with a flat arrangement of electrodes on an uneven surface of the medium. Furthermore, this arrangement may be less sensitive toward tilted placement of the electrodes on the surface of the medium.

Preferably, the locating appliance furthermore comprises a device for controlling the amplitude of the signal from the third AC voltage source such that an alternating current flowing from the opposing electrode into the medium has an absolute value that corresponds to that of an alternating current flowing from the measurement electrode into the medium. This allows further improvement of the compensation described.

The locating appliance may furthermore comprise a further opposing electrode and a fourth AC voltage source for applying to the further opposing electrode a signal that is in antiphase with the voltage on the reference electrode and has an amplitude that is proportional thereto.

The advantages described above may thus likewise be provided for the reference electrode. In this embodiment, a device for controlling the amplitude of the signal from the fourth AC voltage source may be provided such that an alternating current flowing from the further opposing electrode into the medium has an absolute value that corresponds to that of an alternating current flowing from the reference electrode into the medium.

The measurement electrode, the reference electrode and the reception electrode may be surrounded by an alternating arrangement of first and second electrodes, with the first electrodes of the arrangement being electrically connected to the measurement electrode and the second electrodes of the arrangement being electrically connected to the opposing electrode.

This also allows the currents from the measurement electrode and from the opposing electrode, in each case into the medium, to be matched to one another, which means that the influence of the user on a measurement, as has been explained above, can be minimized.

In a further preferred embodiment, the electrodes are situated in one plane and a shielding electrode that is connected to a constant potential and completely covers at least the measurement electrode is arranged on a side that is averted from the object. In this way, the measurement capacitance may be less influencable by an object that is situated on the side that is averted from the medium, particularly by a user of the locating appliance.

For evaluation purposes, the locating appliance may comprise a bridge measurement circuit for detecting the object on the basis of a ratio between the measurement capacitance and the reference capacitance. In particular, a quotient of a difference and a sum can be determined from the reference and measurement capacitances and evaluated. Influences that relate to the measurement capacitance and the reference capacitance in equal measure, for example an ambient temperature or an ambient humidity, are thus unable to influence the measurement.

In a particularly preferred embodiment, the locating appliance has two AC voltage sources in antiphase, the first of which is connected to the measurement electrode and the second of which is connected to the reference electrode, and furthermore a control device for controlling amplitudes of at least one of the AC voltages in order to match the influences of electrical fields from the measurement electrode and the reference electrode on the reception electrode to one another.

Such an evaluation circuit can be used easily and inexpensively in the form of a known integrated circuit.

BRIEF DESCRIPTION OF THE DRAWINGS

The disclosure is now described more precisely with reference to the appended figures, in which.

DETAILED DESCRIPTION

Figure 1A:
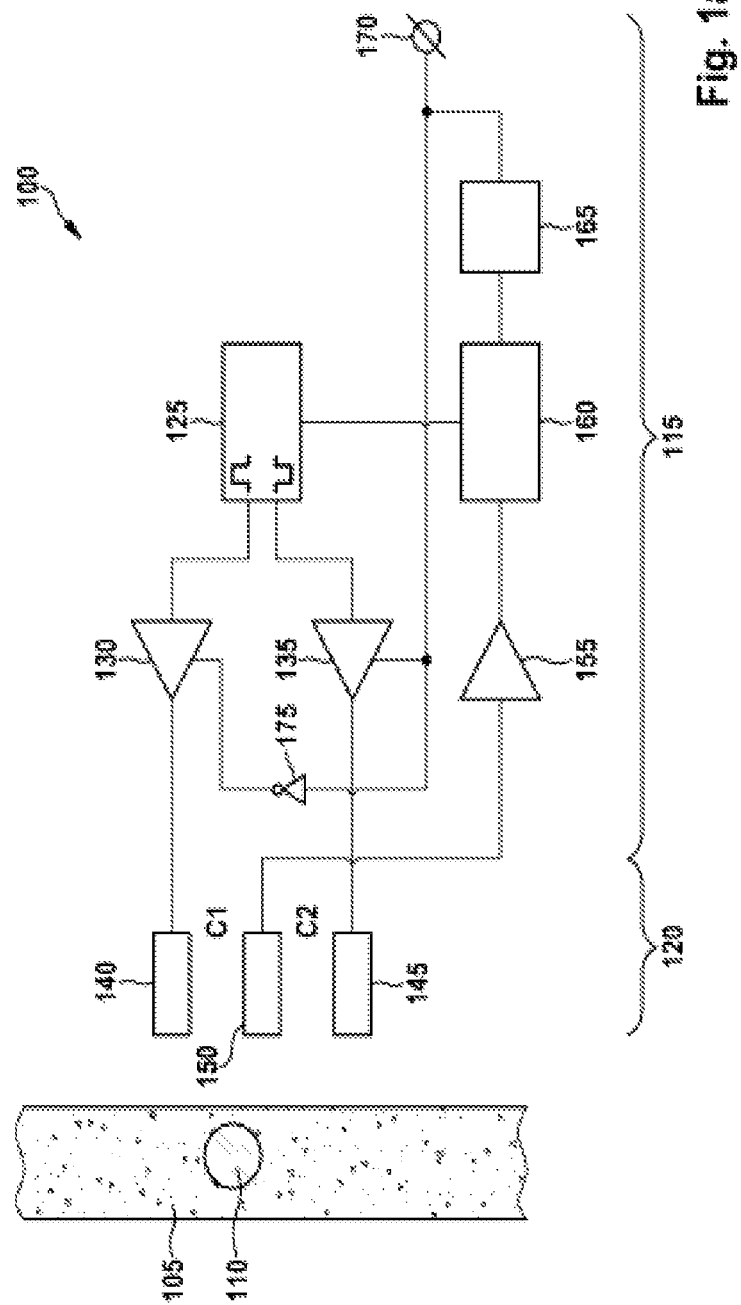
FIG. 1a shows a locating appliance with a first evaluation circuit.

FIG. 1A shows a locating appliance 100 for the capacitive detection of an object 110 enclosed in a medium 105. The locating appliance 100 comprises a push-pull measurement bridge 115 and an arrangement 120 of electrodes.

An oscillator 125 provides two phase-shifted AC voltages, preferably in antiphase, at the same frequency on the measurement bridge 115. The two AC voltages are routed to two amplifiers 130 and 135, at least one of which can have its gain factor controlled by means of a signal. The output of the first amplifier 130 is connected to a measurement electrode 140 and the output of the second amplifier 135 is connected to a reference electrode 145.

The arrangement 120 comprises at least the electrodes 140 and 145 and also a ground-free reception electrode 150. The electrodes 140, 145 and 150 are arranged relative to one another such that a measurement capacitance C1 becomes established between the measurement electrode 140 and the reception electrode 150 and a reference capacitance C2 becomes established between the reference electrode 145 and the reception electrode 150. In this case, the electrodes 140, 145 and 150 are designed such that the measurement capacitance C1 can be influenced by the object 110, whereas the reference capacitance C2 cannot, or can to a negligibly small extent.

The reception electrode 150 is connected to a measurement amplifier 155, the output of which is connected to a synchronous demodulator 160. On the basis of a clock signal that is provided by the oscillator 125 and the frequency of which corresponds to that of the AC voltages that are provided for the amplifiers 130 and 135, the influences of the measurement electrode 140 and the reference electrode 145 on the reception electrode 150 are determined at alternate times and provided for an integrator 165, which may be in the form of an integrating comparator, for example. An output of the integrator 165 is connected to an interface 170 at which a measurement signal is provided. Furthermore, the measurement signal is used to control the gain factors of at least one of the amplifiers 130 and 135. If both amplifiers 130, 135 are controllable, an inverter 175 is provided in order to control the gain factors in opposite directions.

The push-pull measurement bridge 115 is set up to apply AC voltages to the measurement electrode 140 and the reference electrode of the arrangement 120 such that the effect of a dielectric influence of the object 110 on the capacitances C1 and C2 at the reception electrode 150 is of equal magnitude. In this case, the reference capacitance C2 is of a physical design such that it cannot or practically cannot be influenced by the object 110. If the object 110 is situated asymmetrically in the region of the electrodes 140, 145, for example, so that the capacitances C1 and C2 are influenced by the object 110 dielectrically to different degrees, the AC voltages have unequally high amplitudes, so that the influences of the measurement electrode 140 and the reference electrode 145 on the reception electrode 150 are the same on average over time. The measurement signal provided at the interface 170 reflects the modulation of the amplifiers 130, 135. If the measurement signal is higher or lower than a predetermined value that corresponds to a nonexistent object 110, it is possible to infer the object 110 from the measurement signal.

Figure 1B:
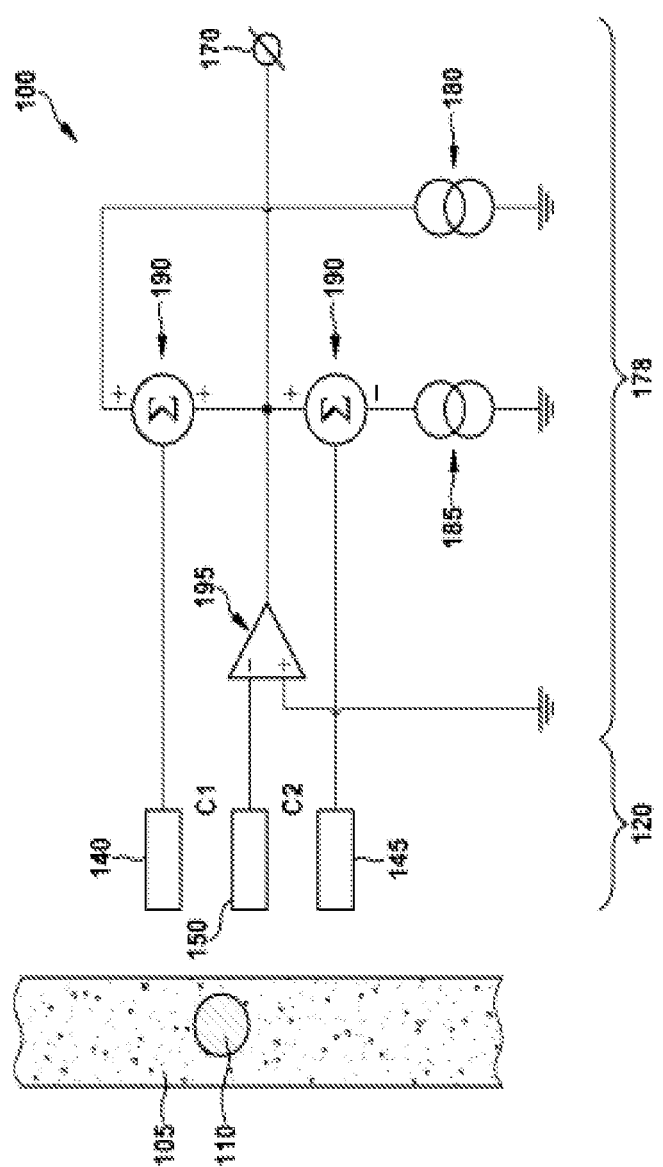
FIG. 1b shows a locating appliance with a second evaluation circuit.

FIG. 1B shows a locating appliance 100 as shown in FIG. 1A, but where the push-pull measurement bridge 115 has been replaced by a bridge measurement circuit 178 with a feedback amplifier.

The measurement electrode 140 is supplied with an AC voltage from a first AC voltage source 180 and the reference electrode 145 is supplied with a second AC voltage from a second AC voltage source 185. The voltages provided by the AC voltage sources 180 and 185 are in antiphase with respect to one another and have the same amplitudes.

The AC voltages from the AC voltage sources 180 and 185 each have an output signal from an amplifier 195 mixed with them by means of a mixer 190, the inverting input of said amplifier being connected to the ground-free reception electrode 150. The output signal from the amplifier 195 and the AC voltage from the first AC voltage source 180 are both mixed together with positive arithmetic signs and forwarded to the measurement electrode 140. For the reference electrode 145, the lower mixer 190 likewise mixes the output signal from the amplifier 195 positively, but mixes the AC voltage from the second AC voltage source 185 negatively, and forwards them to the reference electrode 145.

As a result, the measurement electrode 140 and the reference electrode 145 have AC voltages in antiphase applied to them, the amplitudes of which, in a similar manner to at the push-pull measurement bridge 115 shown in FIG. 1, are controlled such that the influences of electrical fields from the electrodes 140 and 145 on the object 110 correspond to one another. The interface 170 is provided with an AC voltage that indicates the object 110 when it exceeds a predetermined value. In this case, the signal applied to the interface 170 is proportional to a quotient of the difference and the sum of the capacitances C1 and C2. The advantage of the circuit shown is that in the stabilized case the reception electrode 150 is at ground in terms of AC voltage and therefore no alternating currents flow between the reception electrode 150 and ground planes.

Figure 2A:
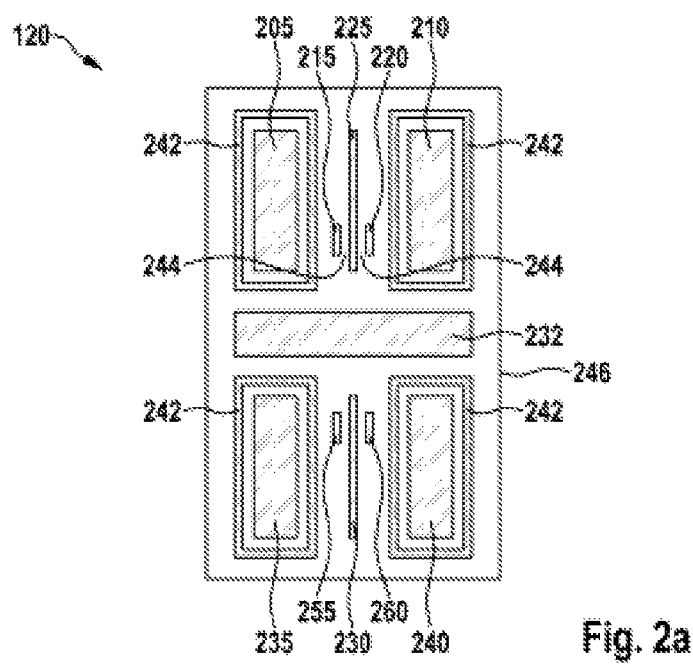
FIG. 2 shows an arrangement of electrodes for the locating appliances in FIGS. 1 and 2.
Figure 2B:
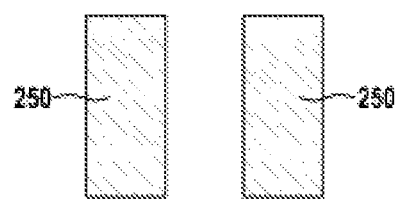
Figure 2B:
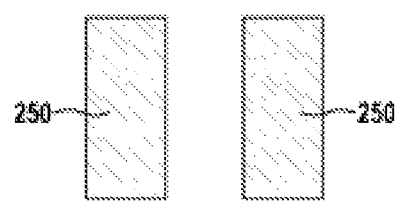

FIG. 2 shows the arrangement 120 of electrodes for the locating appliance 100 from FIG. 1. In this case, FIG. 2A shows electrodes in a first plane, which faces the object 110, and FIG. 2B shows an arrangement of electrodes in a second plane, which is averted from the object 110 in relation to the first plane. In practice, the arrangement shown may be in the form of a printed circuit on different layers of a board made of insulating material, for example.

In FIG. 2A, the first plane contains a first measurement electrode 205 and a second measurement electrode 210, which each correspond to the measurement electrode 140 in FIG. 2, a first reference electrode 215 and a second reference electrode 220, which each correspond to the reference electrode 145 from FIG. 1, and a reception electrode 225, which corresponds to the reception electrode 115 from FIG. 1, and a guard electrode 242. Mutually corresponding electrodes 205 and 210, 215 and 220 may be electrically connected to one another at low impedance. In another embodiment, mutually corresponding electrodes 205-220 have signals applied to them that are the same or not the same but proportional to one another and that may come from different sources. For this purpose, a dedicated amplifier 130 may be provided in the measurement bridge 115 from FIG. 1 for each of the measurement electrodes 205 and 210, for example. Each of the duplicate electrodes 205 and 210, 215 and 220 may also be in single form.

Optionally, the arrangement 120 furthermore contains a first opposing electrode 235 and possibly also one or more further opposing electrodes 240, 255, 260. The measurement electrodes 205, 210 and the opposing electrodes 235, 240 are preferably at the same magnitude and are arranged horizontally and vertically at intervals of the same magnitude from one another. The measurement electrodes 205 and 210 and also the opposing electrodes 235 and 240 may each be surrounded by a guard electrode 242. The reference electrodes 215, 220 and the opposing electrodes 255, 260 are preferably of the same magnitude and arranged horizontally and vertically at intervals of the same magnitude from one another.

Approximately in the center of FIG. 2a there runs a guard electrode 232 in a horizontal direction, isolating the measurement electrodes 205 and 210 arranged at the top, the respective associated guard electrodes 242, the reference electrodes 215 and 220 and the first reception electrode 225 from the opposing electrodes 235, 240, 255 and 260 arranged at the bottom with their associated guard electrodes 242 and the further guard electrode 230. That portion of the arrangement 120 that is situated below the horizontal guard electrode 232 in FIG. 2A can also be omitted in other embodiments.

All of the guard electrodes 230, 232, 242 are optional. The guard electrodes 242 are used to interrupt capacitive couplings between electrodes 205-225, 235, 240 situated in the first plane. The guard electrode 230 corresponds to the reception electrode 150 and increases the symmetry of the electrode arrangement and hence of the field line distribution. The guard electrodes 230, 232, 242 are connected to a predetermined potential, particularly one that is constant over time, for example to an appliance ground of the locating appliance 100 from FIG. 1. This approach differs from known active shielding in that the potential of the guard electrodes is constant over time and is not tracked to another potential. The guard electrodes 230, 232, 242 are particularly suitable when the push-pull measurement bridge 115 shown in FIG. 1 is used, since the measurement bridge 115 is set up to adjust the potential on the reception electrode 150 such that AC voltage components that are in sync with the clock of the AC voltages on the measurement electrode 140 and the reference electrode 145 disappear.

Insulation between adjacent electrodes in the first plane can also be provided by means of air by virtue of a recess 244 being introduced between the electrodes, as shown by way of example between the first reference electrode 215 and the first reception electrode 225 and between the second reference electrode 220 and the first reception electrode 225.

In the preferred embodiment shown, all of the electrodes 205-242 of the arrangement 120 are covered by an insulating layer 246 in order to hamper resistive coupling to the medium 105 of the ambient air or to another object. The insulating layer is also used as a moisture barrier, so that moisture, for example from the air, cannot get into the support material and influence the capacitances.

FIG. 2B shows four shielding electrodes 250, which are each proportioned and positioned such that they cover one of the measurement electrodes 205, 210 or one of the opposing electrodes 235, 240 together with the possibly associated guard electrode 242. The shielding electrodes 250 are connected at the locating appliance 100 to a potential that is constant over time and that may correspond to an appliance ground of the locating appliance 100. In addition or alternatively, the shielding electrodes 250 may be connected to the guard electrodes 242. The shielding electrodes 250 may also be protected from external influences by means of an insulating layer 246—not shown.

Figure 3:
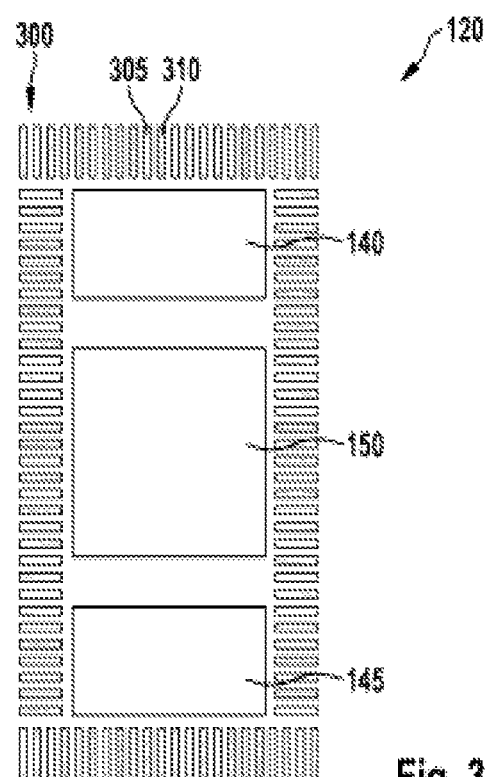
FIG. 3 shows an interdigital electrode for locating appliances in FIGS. 1 and 2.

FIG. 3 shows an interdigital electrode 300 for the locating appliances 100 in FIGS. 1 and 2. The interdigital electrode 300 comprises a multiplicity of first electrodes 305 and second electrodes 310 that are arranged alternately. All the first electrodes 305 are electrically connected to one another and all the second electrodes 310 are electrically connected to one another. In this case, the interdigital electrode 300 surrounds the complete arrangement 120 of electrodes with the possible exception of the shielding electrode 250. FIG.

3 shows only the measurement electrode 140, the reference electrode 145 and the reception electrode 150 from the arrangement 120. Ratios of magnitudes and intervals for the three electrodes 140 to 145 shown are purely exemplary.

The first electrodes 305 are electrically connected to the measurement electrode 140 and the second electrodes 310 are electrically connected to one of the opposing electrodes 235, 240 from FIG. 2.

Figure 4:
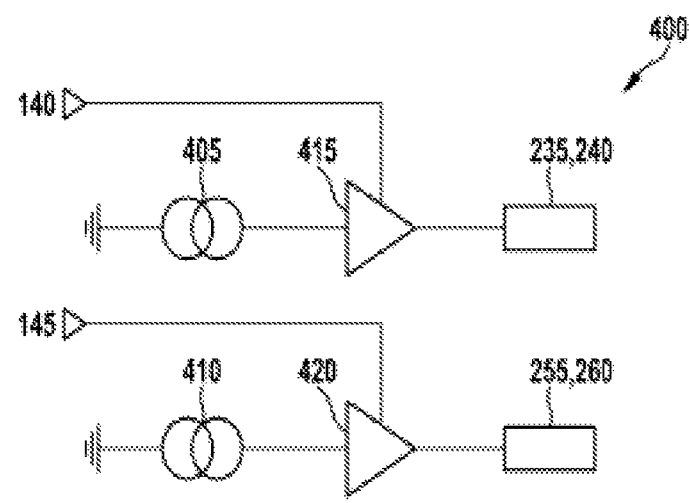
FIG. 4 shows an actuating circuit for the opposing electrodes of the arrangement in FIG. 2.

FIG. 4 shows an actuating circuit 400 for the opposing electrodes 235, 240, 255 and 260 of the arrangement 120 from FIG. 2. The actuating circuit 400 comprises two AC voltage sources 405 and 410, and also two amplifiers 415 and 420. The AC voltage source 405 provides a signal that is in antiphase with the voltage on the measurement electrode 140 and has an amplitude that is proportional to this voltage. Correspondingly, the AC voltage source 410 provides a signal that is in antiphase with the voltage on the reference electrode 145 and has an amplitude that is proportional to this voltage.

In one embodiment, the amplifiers 415 and 420 are dispensed with, and the voltages provided by the voltage sources 405 and 410 are connected directly to the opposing electrodes 235 and 240, and 255 and 260. In another embodiment, which is shown in FIG. 4, the amplifiers 415, 420 or corresponding components such as mixers or controllable attenuation elements are provided in order to control the amplitudes of the AC voltages on the opposing electrodes 235, 240, 255 and 260 such that the absolute value of the alternating current flowing through the first opposing electrode 235 and second opposing electrode 240 corresponds to that of the alternating current flowing through the measurement electrode 140 and the absolute value of the alternating current flowing through the third opposing electrode 255 and fourth opposing electrode 260 corresponds to that of the alternating current flowing through the reference electrode 145. To this end the amplifiers 415 and 420 are suitably connected to the electrodes 140 and 145 or the supply lines thereof, as indicated by the arrows on the connections.

If only the opposing electrodes 235, 240 are provided, that portion of FIG. 4 that corresponds to the further opposing electrodes 255, 260 can be dispensed with.

In a further embodiment, the separate actuating unit for the opposing electrodes 235, 240, 255 and 260 is dispensed with. In that case, the opposing electrodes 235, 240 are directly electrically connected to the reference electrode 145 and the opposing electrodes 255, 260 are directly electrically connected to the measurement electrode 140.

The invention claimed is:

1. A locating appliance for a capacitive detection of an object enclosed in a medium, the locating appliance comprising:
   a measurement electrode configured to induce a first alternating current in the medium;
   a first opposing electrode, the first opposing electrode being configured to induce a second alternating current in the medium that is in antiphase with the first alternating current, the second alternating current having an amplitude that corresponds to an amplitude of the first alternating current;
   a reception electrode configured to form a measurement capacitance with the measurement electrode, the measurement capacitance being influenced by a presence of the object, the reception electrode being further configured to form a reference capacitance that is unaffected by the presence of the object.

2. The locating appliance as claimed in claim 1, further comprising:
   a reference electrode, the reference electrode being configured to induce a third alternating current in the medium,
   wherein the reference capacitance is formed from the reference electrode and the reception electrode.

3. The locating appliance as claimed in claim 2:
   a first voltage source connected to the measurement electrode, the first voltage source being configured to drive the measurement electrode to induce the first alternating current in the medium;
   a second voltage source connected to the first opposing electrode, the second voltage source being in antiphase with the first voltage source and configured to drive the first opposing electrode to induce the second alternating current in the medium; and
   a third voltage source connected to the reference electrode, the third voltage source being in antiphase with the first voltage source and configured to drive the reference electrode to induce the third alternating current in the medium.

4. The locating appliance as claimed in claim 3 further comprising:
   a first device configured to control second voltage source such that the amplitude of the second alternating current corresponds to the amplitude of the first alternating current.

5. The locating appliance as claimed in claim 3 further comprising:
   a second opposing electrode, the second opposing electrode configured to induce a fourth alternating current in the medium that is in antiphase with the third alternating current, the fourth alternating current having an amplitude that corresponds to an amplitude of the third alternating current; and
   a fourth voltage source connected to the second opposing electrode, the fourth voltage source being in antiphase with the third voltage source and configured to drive the second opposing electrode to induce the fourth alternating current in the medium.

6. The locating appliance as claimed in claim 5 further comprising:
   a second device configured to control the fourth voltage source such that the amplitude of the fourth alternating current corresponds to the amplitude of the third alternating current.

7. The locating appliance as claimed in claim 5 further comprising:
   a shielding electrode connected to a constant potential, the shielding electrode at least partially covering the measurement electrode, the reference electrode, the reception electrode, the first opposing electrode, and the second opposing electrode, the shielding electrode being positioned on a side of the locating appliance that is averted from the object,
   wherein the measurement electrode, the reference electrode, the reception electrode, the first opposing electrode, and the second opposing electrode are arranged in a common plane.

8. The locating appliance as claimed in claim 3 further comprising:
   a control device configured to control at least one of the first voltage source and the third voltage source to match a first influence of electrical fields from the measurement electrode on the reception electrode to a second influence of electric fields from the reference electrode on the reception electrode.

9. The locating appliance as claimed in claim 2 further comprising:
a plurality of first electrodes and a plurality of second electrodes, the measurement electrode, the reference electrode, and the reception electrode being surrounded by an alternating arrangement of the first electrodes and the second electrodes, the first electrodes of the alternating arrangement being electrically connected to the measurement electrode and the second electrodes of the alternating arrangement being electrically connected to the reference electrode.

10. The locating appliance as claimed in claim 1, wherein the first opposing electrode forms a capacitance with the medium and is further configured to induce the second alternating current in the medium capacitively.

11. The locating appliance as claimed in claim 1, wherein the first opposing electrode is resistively coupled to the medium and is further configured to induce the second alternating current in the medium resistively.

12. The locating appliance as claimed in claim 1 further comprising:
a bridge measurement circuit configured to detect the object based at least in part on a ratio between the measurement capacitance and the reference capacitance.

13. A locating appliance for a capacitive detection of an object enclosed in a medium, the locating appliance comprising:

a measurement electrode, the measurement electrode being driven by a first voltage source configured to induce a first alternating current in the medium;

a first opposing electrode, the first opposing electrode being driven by a second voltage source, the second voltage source being in antiphase with the first voltage source and configured to induce a second alternating current in the medium, the second alternating current having an amplitude that corresponds to an amplitude of the first alternating current;

a reference electrode, the reference electrode being driven by a third voltage source, the third voltage source being in antiphase with the first voltage source and configured to induce a third alternating current in the medium; and a reception electrode configured to form a measurement capacitance with the measurement electrode and form a reference capacitance with the reference electrode, the measurement capacitance being influenced by a presence of the object, the reference capacitance being unaffected by the presence of the object.

* * * * *